US00PP12898P2

(12) United States Plant Patent
Domoto

(10) Patent No.: US PP12,898 P2
(45) Date of Patent: Sep. 3, 2002

(54) WALNUT TREE NAMED 'DOMOTO'

(75) Inventor: Paul Alan Domoto, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/442,432

(22) Filed: Nov. 17, 1999

(51) Int. Cl.[7] ..... A01H 5/00
(52) U.S. Cl. ..... Plt./154
(58) Field of Search ..... Plt./154

(56) References Cited

PUBLICATIONS

Paul A. Domoto, Selecting Carpathian Walnuts (*juglans regia L.*) for Cold Hardiness; Journal Paper No. J–12383 of the Iowa Agriculture and Home Economics Experiment Station, Ames IA; Project No. 1945; Pub. 1986.
L. C. Stephans et al., In Vitro Propagation of *Juglans regia*, 'ISU71–3–18', Pub. 1991.

*Primary Examiner*—Bruce R. Campell
*Assistant Examiner*—A Para
(74) *Attorney, Agent, or Firm*—Dickstein Shapiro Morin & Oshinsky LLP

(57) ABSTRACT

A cold-resistant Persian walnut cultivar originating as an open pollinated seedling from a population of seedlings, for which the identity of the female parent was not recorded, that were planted at the Iowa State University Horticulture Research Farm, Ames, Iowa, USA in 1971, and evaluated as ISU71-EI8. Past literature and growth characteristics suggest that one of the parents was probably 'Hansen' (unpatented) Persian walnut. The other parent may have been 'Colby' (unpatented) Persian walnut. Tree has consistently exhibited minimal shoot die-back when exposed to late-fall/early-winter, mid-winter, and late-winter freezes; when exposed to minus 35.6 degrees Celsius, trees suffered only minor to moderate shoot die-back while other cultivars and selections were killed or severely injured. Catkin survival has been recorded following expose to minus 32 degrees Celsius. Tree is small, slow growing, moderately vigorous; globular in shape with a somewhat upright branching habit; leafs out early, and defoliates relatively late. Catkins are medium sized; abundant; release pollen mid-season, about 5 days after first pistillate flowers are receptive. Pistillate flowers occur mostly as doubles produced terminally on spurs with some produced laterally on shoots; receptive early mid-season with about a 10 day overlap of staminate and pistillate bloom; considered partially dichogamous and does best with cross pollination. Fruit: ripen in late-September to early-October; nut roundish oblong, compressed, slightly to moderately beaked and rounded at base; medium size (101 nuts per kilogram, 46 per pound); shell thin, moderately hard, well sealed, relatively smooth; cavity well filled, kernel tight and difficult to remove in halves; kernel moderately small to medium sized, plump, richly flavored, oily, somewhat astringent, quality good. Productivity low with out cross pollination, medium with cross pollination. Suitable as a nut producing ornamental in nothern climates where commercial cultivars cannot be grown. Adapted to zones 5a and 4b of the USDA Plant Hardiness Zone Map.

5 Drawing Sheets

FIELD OF THE INVENTION

This invention pertains to a new and distinct cultivar of Persian walnut (*Juglans regia*) tree adapted to northern growing climates of the U.S.A. designated on the USDA Plant Hardiness Zone Map as Zone 5a and Zone 4b. The nuts are a smaller size than eating nuts commercially-produced in California and Oregon. The tree is small in stature and is adapted to colder climates. The present walnut tree is most suited as an ornamental or a non-commercial walnut producer, unless medium to small walnuts become desirable by consumers in the future.

DESCRIPTION OF DEVELOPMENT

The tree originated from a collection of open pollinated nuts collected and germinated by hobbyist nut growers from unpatented Persian walnut trees growing in central and eastern Iowa, U.S.A. for which the identity of the female parent was not recorded. The collection of trees were planted at the Iowa State University Horticulture Farm, Ames, Iowa, U.S.A. in 1971 by Mr. Allen R. Beck. Each of the trees were designated by row letter and tree number in the row, and were evaluated for resistance to low winter temperatures along with several unpatented Persian walnut cultivars grafted on unpatented eastern black walnut (*Juglans nigra*). The tree presently claimed was designated and tested as ISU71-E18 in the selection process. The present inventor assumed responsibility for the project in 1975, and subsequently identified the claimed tree in 1986 as one which exhibited outstanding hardiness characteristics compared to other selections or the grafted cultivars.

Following recognition that ISU71-E18 had outstanding hardiness characteristics, it was asexually propagated by topworking onto an established unpatented eastern black walnut (*Juglans nigra*) tree in 1988, and budded on unpatented eastern black walnut rootstock in 1989 and lined out in the field in 1990. The resulting trees were true to the parent in all respects including general appearance, shape, branching, leaves, flowering, fruit, and resistance to low winter temperatures.

Past literature and growth characteristics of the claimed tree suggest that one of the parents was probably unpatented 'Hansen', and possibly unpatented 'Colby' Persian walnuts. In 1972, Beck reported that the 73 trees planted in 1971 were supplied by Frank Kosek, Cedar Rapids, Iowa, USA (10); Frank Martzahn, Davenport, Iowa, USA (3); and Archie Sparks, Beaver, Iowa, USA (60). Mr. Sparks (personnel communication) revealed that the trees he supplied originated from nuts obtained from a collection of Persian walnut trees growing in Huxley, Iowa, U.S.A. that were established by Mr. Steward Burhow. In 1964, Burhow reported that 'Hansen' and 'Colby' were his most productive trees, and that 'Hansen' had a tendency to produce nuts that "turned black and remained unfilled." Other unpatented Persian walnut trees grown by Mr. Burhow were 'Broadview', 'R24T1', and 'Caeser'.

'Hanson' was discovered in Clay Center, Ohio, USA by the father of Awalt Hansen. It was selected in 1934 and introduced in 1950. Seed that produced the tree is considered to be of German origin. Nuts are small to medium (58 nuts per pound), round; thin shelled; mild flavor, sweet, good; kernel percentage high (60%). Tree is small, essentially dwarf, and bears early. It is the most widely planted, winter hardy cultivar.

In comparison to 'Hansen', the claimed tree is similar in stature and hardier; produces larger nuts; similar in earliness of bearing; and has a tendency to produce "blank" nuts.

'Colby' originated in Urbana, Ill. by A.S. Colby, Illinois Agricultural Experiment Station, from an open pollinated seedling of unpatented 'Crath 10' (Carpathian type seed from Cosseev, Poland obtained in 1934), and was introduced in 1952. Nut is of medium size, thin shelled, well-sealed; 53% kernel that is plump, good flavor and matures early. Tree is not considered as hardy as other Persian walnut cultivars recommended for northern climates.

In comparison with 'Colby', the claimed tree produces nuts of similar size, shape, and kernel percentage, but is more hardy to cold temperatures.

'Broadview' originated in Westbank, British Columbia, Canada, from seed brought from Odessa Russia by the family of J.U. Gellatly, and was introduced in 1930. Nuts are medium to large, oblong, soft shelled, well sealed, 47% kernal. Tree is hardy and productive.

In comparison with 'Broadview', the claimed tree produces smaller nuts of a different shape. The nuts of the claimed tree are rounder and larger than the nuts of 'Broadview'.

'R24T1', although not known to be cultivated at the present time, was an unreleased, open pollinated Carpathian walnut seedling that originated from seed collected in 1936 in eastern Europe and shipped out of the Ukraine by Reverand Paul C. Crath. The seeds were distributed by the Wisconsin Horticulture Society in 1939 to the Tennessee Valley Authority and grown in a plantation at Norris, Tenn. The nuts were said to be of good size.

Little is known of 'R24T1', but based on historical accounts, the nuts were larger than produced by the claimed tree.

'Caesar' was introduced in 1938 and originated in Roanoke, Va. by Harvey F. Stike from Carpathian-type walnut seed. The seed was imported by Paul Crath from Poland. Nuts are very large, very thin shelled; kernel is of good quality, but sometimes does not fully develop.

In comparison to 'Caesar' the claimed tree produces smaller sized nuts with slightly thicker shells.

SUMMARY OF THE INVENTION

A new and distinct cultivar of Persian walnut (*Juglans regia*) tree, as herein described and illustrated and characterized by being a hardy tree of a small size, slow growing with somewhat upright branches producing a globular shaped tree that is almost as broad as it is high, having a moderate to dense foliage, pinnately compound leaves with 7 to 9 elliptical leaflets, that bears fruit early predominately on the terminal of spurs with a portion of the crop produced laterally on shoots. Catkin buds withstand exposure to minus 26 degrees Fahrenheit, and trees have withstood minus 32 degrees Fahrenheit with minimal shoot injury. Produces medium size, thin-shelled, well-sealed nuts with plump, flavorful, mildly bitter, light colored kernels.

'Stark® Northern Prize (Domoto)' is advantageous over 'Hansen' in that it produces larger nuts, although some are blank as in 'Hansen'.

'Stark® Northern Prize (Domoto)' is advantageous over 'Colby' in that it is more winter hardy.

BOTANICAL DESCRIPTION OF THE PLANT

Figure 1:
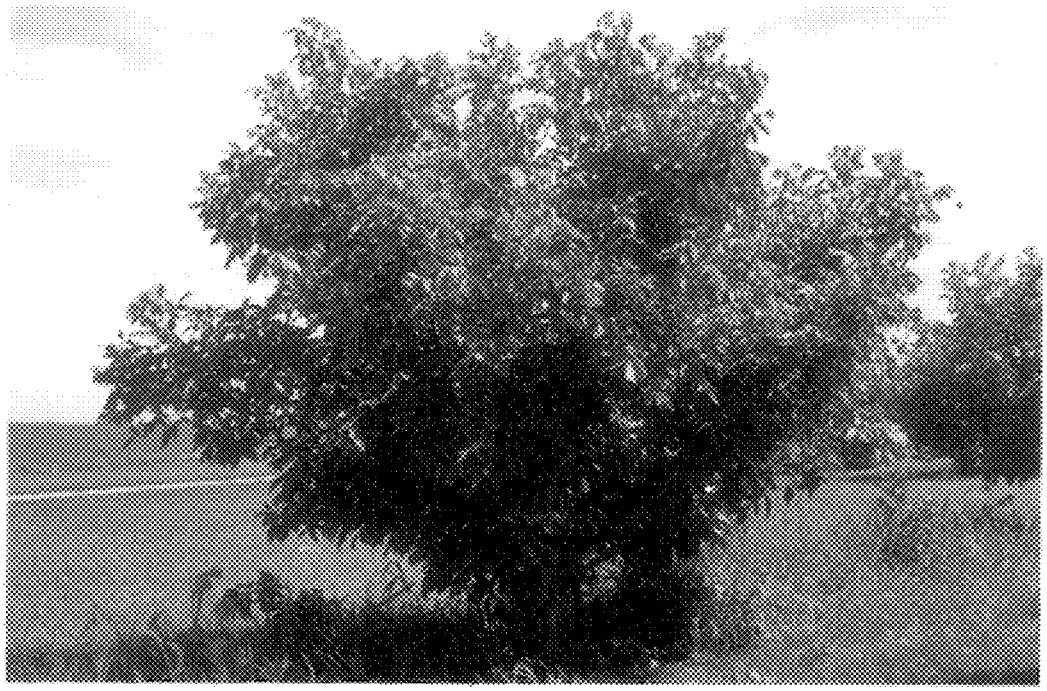
FIG. 1 shows parent tree in fifteenth season of growth.

The botanical details of this new and distinct cultivar of Persian walnut tree — with color definitions (except those in common color terms) referenced to The Royal Horticultural Society, London, *R.H.S. Colour Chart* — are as follows:

Tree: Hardy; consistently exhibits minimal shoot die-back when exposed to late-fall/early-winter, mid-winter, and late-winter freezes; when exposed to −32 degrees F., trees suffered only minor to moderate shoot die-back while other cultivars and selections were severely injured. Small sized, almost dwarf in comparison to the size attainable for the species; slow growing, moderately vigorous. Form/shape globular, with spread almost equaling the height.

Trunk: Stout; bark texture smooth; color grayish-white (156C).

Branches: Stocky; smooth textured bark with numerous, white, spherical to elliptical, raised lenticels. Branching habit somewhat upright. Color: new wood yellow-green (144B), glossy; mature wood brown (200C), glossy. Foliage abundant, moderately dense; time of leafing out early; time of defoliation relatively late.

Leaves: Pinnately compound with 7 to 9 leaflets; large sized ranging from 8 to 14 inches in length. Leaflets elliptic, varying from 2 to 7 inches in length, and 1 to 5 inches in width; moderately thick, leathery, rugose, and glabrous; margins glabrous. Color: Top side yellow-green (147B);

bottom side a lighter green (yellow-green 147C). Petiole long tapering, and stout; glands and stipules wanting.

Flowering habit: Monoecious.

Catkins: Medium sized; hardy with survival of dormant catkins recorded following expose to −26 degrees F. while catkins on other cultivars and selections were killed. Young, asexually propagated trees initiated catkins in the fifth growing season to release pollen during the sixth growing season. Catkin production is moderate on young trees, and abundant on mature trees. Pollen release mid-season; first release averages 5 days (2 to 9 day range) after first pistillate flowers are receptive; duraton 13 day average (7 to 24 day range).

Pistillate flowers: Occur mostly as doubles produced terminaly on spurs, some (less than 10%) produced laterally on longer shoots. Presence of pistillate flowers on young trees observed in the forth growing season; moderately abundant on young trees, abundant on mature trees. Time of first pistillate flower receptivity early mid-season [on average, 7 days (3 to 10 day range) after full bloom of 'Delicious' apple (*Malus domestica*)]; average duration 15 days (10 to 26 day range) with flowers produced terminally on spurs blooming ahead of those produced laterally on shoots. Coincidence of staminate and pistillate bloom averages 10 days (5 to 19 day range); considered partially dichogamous and does best with an early pollen shedding cultivar.

Crop: Bears regularly; productivity low without cross pollination, medium with cross pollination; tendency to carry parthenocarpic fruit almost to maturity. Ripens in late September to early October.

Fruit: Subglobose and sutured; medium sized. Hull fleshy, smooth, glabrous, yellow-green (144A) with numerous conspicuous white dots; moderately thick; dehiscent, opening from apex to base in no particular pattern.

Nut: Roundish oblong, compressed (average: length 1.44"; check to check 1.37"; suture plane 1.20"); apex slightly to moderately beaked; basal end rounded; medium sized (46 nuts per pound).

Shell: Thin, moderately hard, well sealed; surface relatively smooth with shallow veins and furrows; color light brown (yellow-orange 22C). Diaphragm moderately thick and rigid, particularly at the basal end. Cavity well filled, kernel tight and difficult to remove in halves.

Kernel: Moderately small to medium sized, plump, convolutions moderate and even. Pellicle light yellowish brown (yellow-orange 22C), semi-glossy, somewhat astringent, some speckling, and lightly veined. Richly flavored, oily; quality good.

Tree appears resistant to disease. Leaves are relatively tolerant to potato leafhopper (*Empoasca fabae*) damage.

The Persian walnut tree and its nuts herein described may vary in slight detail due to climate and soil conditions under the cultivar may be grown; the present description being of the cultivar as grown in Ames, Iowa.

I claim:

1. A new and distinct, cold-resistant cultivar of Persian walnut tree named 'Domoto' substantially as shown and described that withstands exposure to minus 35.6 degrees Celsius with minimal shoot injury, produces catkins that withstand exposure to minus 32 degrees Celsius, that is of small stature, and produces, on average, nuts that are larger than those produces by 'Hansen' (unpatented) Persian walnut.

* * * * *

UNITED STATES PATENT AND TRADEMARK OFFICE

CERTIFICATE OF CORRECTION

PATENT NO. : PP 12,898 P2
DATED : September 3, 2002
INVENTOR(S) : Domoto

It is certified that error appears in the above-identified patent and that said Letters Patent is hereby corrected as shown below:

Delete columns 1 to 6 and substitute therefore columns 1 to 6. (as shown on attached sheets)

Signed and Sealed this

Twenty-eighth Day of October, 2003

JAMES E. ROGAN
*Director of the United States Patent and Trademark Office*

(12) United States Plant Patent
Domoto

(10) Patent No.: US PP12,898 P2
(45) Date of Patent: Sep. 3, 2002

(54) WALNUT TREE NAMED 'DOMOTO'

(75) Inventor: Paul Alan Domoto, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/442,432

(22) Filed: Nov. 17, 1999

(51) Int. Cl.[7] ..... A01H 5/00
(52) U.S. Cl. ..... Plt./154
(58) Field of Search ..... Plt./154

(56) References Cited

PUBLICATIONS

Paul A. Domoto, Selecting Carpathian Walnuts (*juglans regia* L.) for Cold Hardiness; Journal Paper No. J–12383 of the Iowa Agriculture and Home Economics Experiment Station, Ames IA; Project No. 1945; Pub. 1986.
L. C. Stephans et al., In Vitro Propagation of *Juglans regia*, 'ISU71–3–18', Pub. 1991.

*Primary Examiner*—Bruce R. Campell
*Assistant Examiner*—A H Para
(74) *Attorney, Agent, or Firm*—Dickstein Shapiro Morin & Oshinsky LLP

(57) ABSTRACT

A cold-resistant Persian walnut cultivar originating as an open pollinated seedling from a population of seedlings, for which the identity of the female parent was not recorded, that were planted at the Iowa State University Horticulture Research Farm, Ames, Iowa, USA in 1971, and evaluated as ISU71-EI8. Past literature and growth characteristics suggest that one of the parents was probably 'Hansen' (unpatented) Persian walnut. The other parent may have been 'Colby' (unpatented) Persian walnut. Tree has consistently exhibited minimal shoot die-back when exposed to late-fall/early-winter, mid-winter, and late-winter freezes; when exposed to minus 35.6 degrees Celsius, trees suffered only minor to moderate shoot die-back while other cultivars and selections were killed or severely injured. Catkin survival has been recorded following exposure to minus 32 degrees Celsius. Tree is small, slow growing, moderately vigorous; globular in shape with a somewhat upright branching habit; leafs out early, and defoliates relatively late. Catkins are medium sized; abundant; release pollen mid-season, about 5 days after first pistillate flowers are receptive. Pistillate flowers occur mostly as doubles produced terminally on spurs with some produced laterally on shoots; receptive early mid-season with about a 10 day overlap of staminate and pistillate bloom; considered partially dichogamous and does best with cross pollination. Fruit: ripen in late-September to early-October; nut roundish oblong, compressed, slightly to moderately beaked and rounded at base; medium size (101 nuts per kilogram, 46 per pound); shell thin, moderately hard, well sealed, relatively smooth; cavity well filled, kernel tight and difficult to remove in halves; kernel moderately small to medium sized, plump, richly flavored, oily, somewhat astringent, quality good. Productivity low with out cross pollination, medium with cross pollination. Suitable as a nut producing ornamental in northern climates where commercial cultivars cannot be grown. Adapted to zones 5a and 4b of the USDA Plant Hardiness Zone Map.

5 Drawing Sheets

FIELD OF THE INVENTION

This invention pertains to a new and distinct cultivar of Persian walnut (*Juglans regia*) tree adapted to northern growing climates of the U.S.A. designated on the USDA Plant Hardiness Zone Map as Zone 5a and Zone 4b. The nuts are a smaller size than eating nuts commercially produced in California and Oregon. The tree is small in stature and is adapted to colder climates. The present walnut tree is most suited as an ornamental or a non-commercial walnut producer, unless medium to small walnuts become desirable by consumers in the future.

DESCRIPTION OF DEVELOPMENT

The tree originated from a collection of open pollinated nuts collected and germinated by hobbyist nut growers from unpatened Persian walnut trees growing in central and eastern Iowa, U.S.A. for which the identity of the female parent was not recorded. The trees were planted at the Iowa State University Horticulture Farm, Ames, Iowa, U.S.A. in 1971 by Mr. Allen R. Beck. Each of the trees were designated by row letter and tree number in the row, and were evaluated for resistance to low winter temperatures along with several unpatented Persian walnut cultivars grafted on unpatented eastern black walnut (*Juglans nigra*). The tree presently claimed was designated and tested as ISU71-EI8 in the selection process. The present inventor assumed responsiblity for the project in 1975, and subsequently identified the claimed tree in 1986 as one that exhibited outstanding hardiness characteristics compared to other selections or tile grafted cultivars.

Following recognition that ISU71-EI8 had outstanding hardiness characteristics, it was asexually propagated by topworking onto an established unpatented eastern black walnut (unpatented) (*Juglans nigra*) tree located at the Iowa State University Horticulture Farm, Ames, Iowa, U.S.A. in 1988, and budded on unpatented eastern black walnut rootstock (unpatented) in 1989 and lined out in the field in 1990. The resulting trees were true to the parent in all respects including general appearance, shape, branching, leaves, flowering, fruit, and resistance to low winter temperatures.

PERTINENT BACKGROUND INFORMATION

Past literature and growth characteristics of the claimed tree suggest that one of the parents was probably 'Hansen'

(unpatented) Persian walnut. The other parent may have been 'Colby' (unpatented) Persian walnut. In 1972, Beck reported that the 73 trees planted in 1971 were supplied by Frank Kosek, Cedar Rapids, Iowa, USA (10 trees); Frank Martzahn, Davenport, Iowa, USA (3 trees); and Archie Sparks, Beaver, Iowa, USA (60 trees). Mr. Sparks (personnel communication) revealed that the trees he supplied originated from nuts obtained from a collection of Persian walnut trees growing in Huxley, Iowa, U.S.A. that were established by Mr. Steward Burhow. In 1964, Burhow reported that 'Hansen' (unpatented) and 'Colby' (unpatented) were his most productive trees, and that 'Hansen' (unpatented) had a tendency to produce nuts that "turned black and remained unfilled." Other patented Persian walnut trees grown by Mr. Burhow were 'Broadview' (unpatented), 'R24TI' (unpatented), and 'Caesar' (unpatented).

'Hanson' (unpatented) Persian walnut was discovered by the father of Awalt Hansen in Clay Center, Ohio, USA. It was selected in 1934 and introduced in 1950. Seed that produced the tree is considered to be of German origin. Nuts are small to medium (128 per kilogram); round; thin shelled; mild flavor, sweet, good; kernel percentage high (60%). Tree is small, essentially dwarf, and bears early. It is the most widely planted, winter hardy cultivar.

In comparison to 'Hansen' (unpatented) Persian walnut, the claimed tree is similar in stature and hardier; produces larger nuts; similar in earliness of bearing; and has a tendency to produce 'blank' nuts.

'Colby' (unpatented) Persian walnut originated in Urbana, Ill. by A. S. Colby, Illinois Agricultural Experiment Station, from an open pollinated seedling of unpatented 'Crath 10' (unpatented) Persian walnut (Carpathian type seed from Cosseev, Poland obtained in 1934), and was introduced in 1952. Nut is of medium size, thin shelled, well-sealed; 53% kernel that is plump, good flavor and matures early. Tree is not considered as hardy as other Persian walnut cultivars recommended for northern climates.

In comparison with 'Colby' (unpatented) Persian walnut, the claimed tree produces nuts of similar size, shape, and kernel percentage, but is more hardy to cold temperatures.

'Broadview' (unpatented) Persian walnut originated in Westbank, British Columbia, Canada, from seed brought from Odessa Russia by the family of J. U. Gellatly, and was introduced in 1930. Nuts are medium to large, oblong, soft shelled, well sealed, 47% kernel. Tree is hardy and productive.

In comparison with 'Broadview' (unpatented) Persian walnut, the claimed tree produces smaller nuts of a different shape. The nuts of the claimed tree are rounder and larger than the nuts of 'Broadview'.

'R24TI' (unpatented) Persian walnut, although not known to be cultivated at the present time, was all unreleased, open pollinated Carpathian walnut seedling that originated from seed collected in 1936 in eastern Europe and shipped out of the Ukraine by Reverend Paul C. Crath. The seeds were distributed by the Wisconsin Horticulture Society in 1939 to the Tennessee Valley Authority and grown in a plantation at Norris, Tenn., U.S.A. The nuts were said to be of good size.

Little is known of 'R24TI' (unpatented) Persian walnut, but based on historical accounts, the nuts were larger than produced by the claimed tree.

'Caesar' (unpatented) Persian walnut was introduced in 1938 and originated in Roanoke, Va., U.S.A. by Harvey F. Stike from Carpathian-type walnut seed imported from Poland by Reverend Paul C. Crath. Nuts are very large, very thin shelled; kernel is of good quality, but sometimes does not fully develop.

In comparison to 'Caesar' (unpatented) Persian walnut the claimed tree produces smaller sized nuts with slightly thicker shells.

SUMMARY OF THE INVENTION

A new and distinct cultivar of Persian walnut (*Juglans regia*) tree, as herein described and illustrated and characterized by being a hardy tree of a small size, slow growing with somewhat upright branches producing a globular shaped tree that is almost as broad as it is high, having a moderate to dense foliage, pinnately compound leaves with 7 to 9 (typically 7) elliptical leaflets, that bears fruit early predominately on the terminal of spurs with a portion of the crop produced laterally on shoots. Catkin buds withstand exposure to minus 32 degrees Celsius, and trees have withstood minus 35.6 degrees Celsius with minimal shoot injury. Produces medium size, thin-shelled, well-sealed nuts with plump, flavorful, mildly bitter, light colored kernels.

Claimed tree is advantageous over 'Hansen' (unpatented) Persian walnut in that it produces larger nuts, although some are blank as in 'Hansen'.

Claimed tree is advantageous over 'Colby' (unpatented) Persian walnut in that it is more winter hardy.

BRIEF DESCRIPTION OF THE DRAWINGS

FIG. 1 shows parent tree in fifteenth season of growth.

Figure 2:
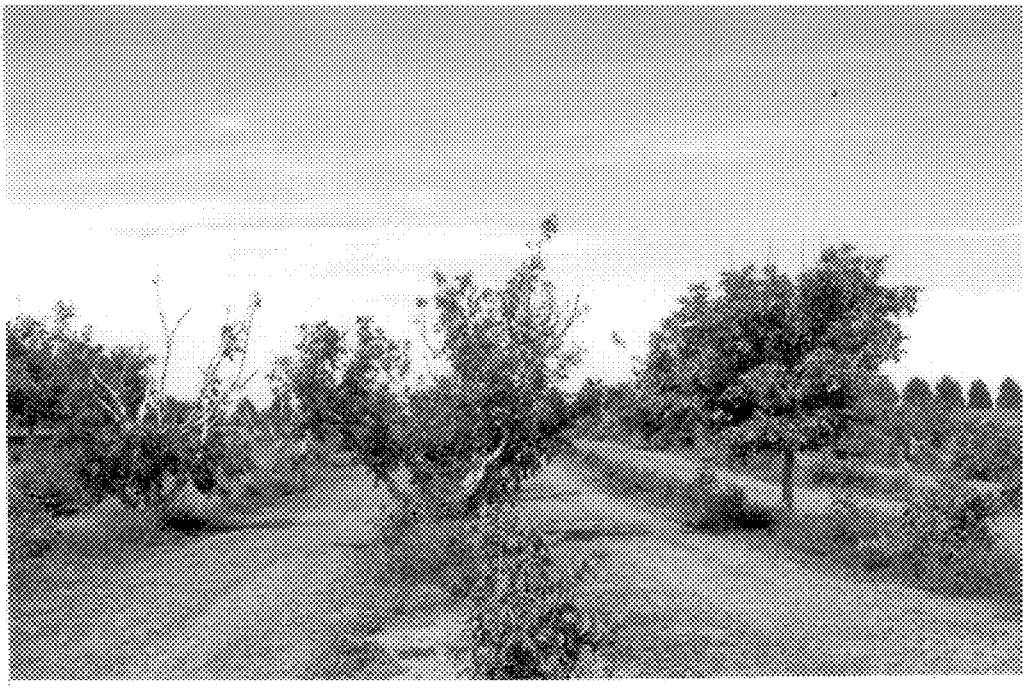
FIG. 2 shows an asexually propagated tree grafted on Eastern black walnut at a height of 5 feet above the ground (right) compared to seedling selections planted in 1973 (larger trees, left) following exposure to −32 degrees F. in 1996.

FIG. 2 shows an asexually propagated tree grafted on Eastern black walnut (unpatented) at a height of 1.5 meters above the ground (right) compared to seedling selections planted in 1973 (larger trees, left) following exposure to minus 35.6 degrees Celsius in 1996.

Figure 3:
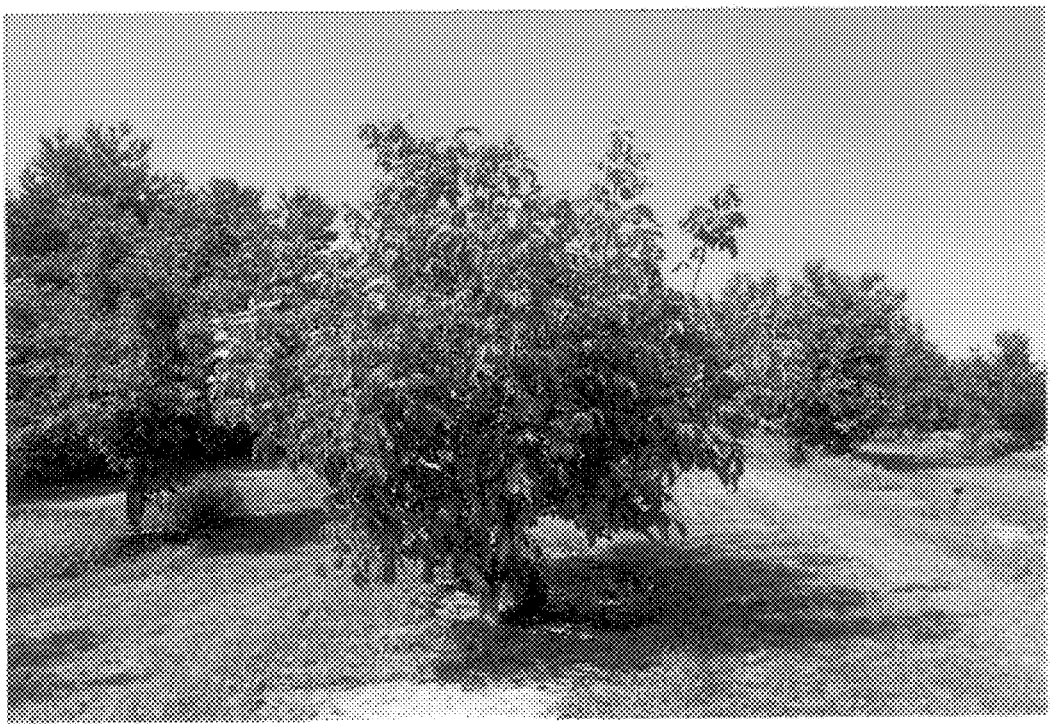
FIG. 3 shows an asexually propagated tree budded on Eastern black walnut in the tenth growing season that has grown to a height of 10 feet, and a spread of 9.2 feet.

FIG. 3 shows an asexually propagated tree budded on Eastern black walnut (unpatented) in the tenth growing season that has grown to a height of 3.0 meters, and a spread of 2.8 meters.

Figure 4:
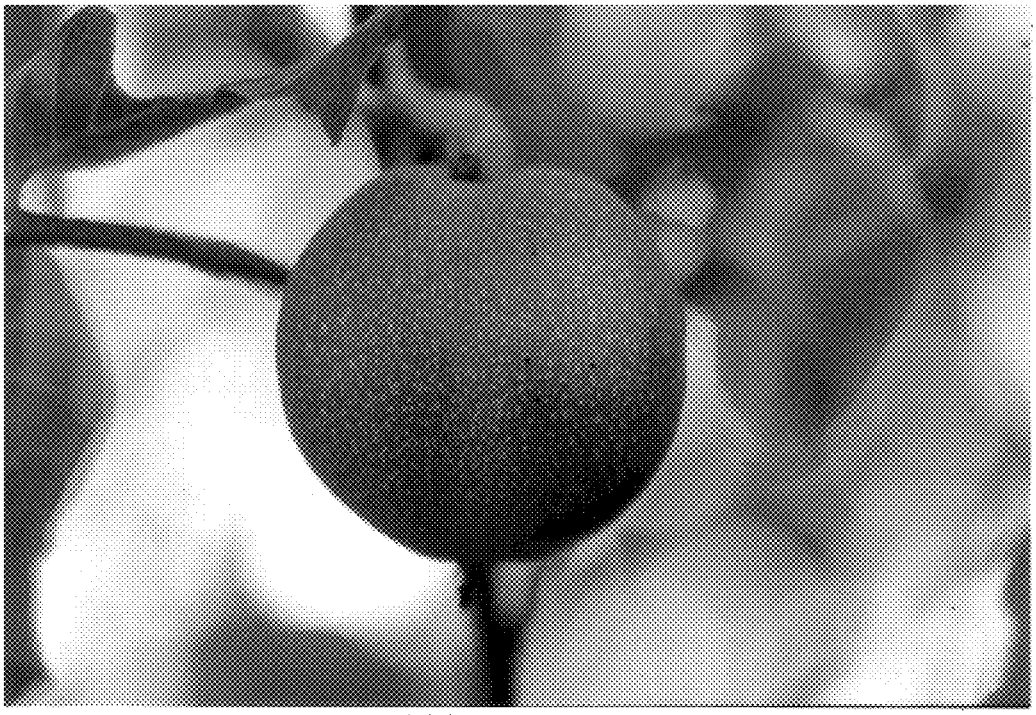
FIG. 4 shows a nut in the hull to illustrate hull color and prominent suture indentation.

FIG. 4 shows a nut in the hull to illustrate hull color and prominent suture indentation.

Figure 5:
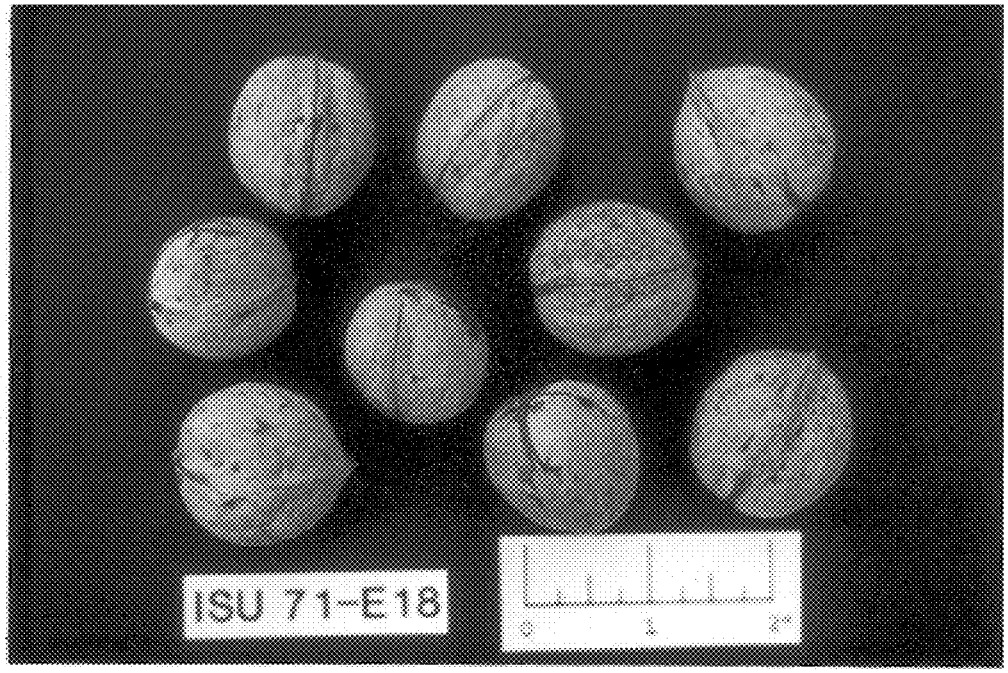
FIG. 5 shows the nuts in the shell to illustrate nut shape, size, and shell color and texture.

FIG. 5 shows the nuts in the shell to illustrate nut shape, size, and shell color and texture.

BOTANICAL DESCRIPTION OF THE PLANT

The botanical details of this new and distinct cultivar of Persian walnut tree were derived from the 23-year-old parent tree before it died in 1994, a 12-year-old instant tree topworked into an established eastern black walnut (unpatented) seedling tree at a height of 1.5 meters, and a 10-year-old instant tree budded into a eastern black walnut (unpatented) seedling rootstock growing at the Iowa State University Horticulture Farm, Ames, Iowa, U.S.A.—with color definitions (except those in common color terms) referenced to The Royal Horticultural Society, London, R.H.S. Colour Chart—are as follows:

Tree: Hardy; consistently exhibits minimal shoot die-back when exposed to late-fall/early-winter, and later-winter, and late-winter freezes; when exposed to minus 35.6 degrees Celsius, trees suffered only minor to moderate shoot die-back while other cultivars and selections were killed or severely injured. Small sized (height and spread; parent tree, approximately 6.0 by 6.0 meters; 12-year-old topworked instant tree, 6.0 by 5.8 meters; 10-year-old budded instant tree, 3.0 by 2.8 meters), almost dwarf in comparison to the size attainable for the species; slow growing, moderately vigorous. Form/shape globular, with spread almost equaling the height.

Trunk: Stout (diameter at 30 centimeters above the ground: parent tree, 43 centimeters; 12-year-old topworked instant tree, 25 centimeters; 10-year-old budded instant tree, 14 centimeters); bark, texture smooth; color grayish-white (156C), dull.

Branches: New shoots; stocky, 9 millimeters at base (range 5 to 13 millimeters), length 6 to 50 centimeters; bark smooth textured, color yellow-green (144B), glossy on developing shoots changing to grayed-orange (165A), glossy as shoots mature; lenticels scattered (averaging 6.6 per square centimeter, range 3 to 16 per square centimeter), raised white, spherical (0.1 to 0.5 millimeter diameter) often coalescing in a vertical plane to appear elliptical (up to 2.0 millimeters long). Branches developing a gray sheen with age and becoming a dull, grayish-white (156C) by fourth year; lenticels expanding in width with age. Branching habit somewhat upright, crotch angles typically 45 degrees (range 30 to 60 degrees); major branches on 12-year old topworked instant tree 10 to 15 centimeters diameter at the base, 2.5 to 4.0 meters long. Foliage abundant, moderately dense; time of leafing out early; time of defoliation relatively late.

Leaves: Pinnately compound with 5 to 9 leaflets (typically 7); large sized ranging from 20 to 30 centimeters in length. Leaflets ellipsoid, terminal leaflet typically 12 centimeters long (range 10 to 15 centimeters) by 6 centimeters wide (range 5.0 to 7.5 centimeters), obtuse at apex and base; lateral leaflets opposite, ranging from 5.0 to 11.0 centimeters long by 2.5 to 5.5 centimeters wide with an obtuse apex and oblique base; pinnately veined, moderately thick, leathery, rugose, and glabrous; margins entire. Color: Top side yellow-green (147B); bottom side a lighter green (yellow-green 147C). Petiole long tapering, and stout; glands and stipules wanting; color yellow-green (151A).

Flowering habit: Monoecious.

Catkins: Medium sized (75×12 millimeters, length by diameter when expanded); hardy with survival of dormant catkins recorded following exposure to minus 32 degrees Celsius while catkins on other cultivars and selections were killed. Young, asexually propagated trees initiated catkins in the fifth growing season to release pollen during the sixth growing season. Catkin production is moderate on young trees, and abundant on mature trees. Pollen release mid-season; first release averages 5 days (range 2 to 9 days) after first pistillate flowers are receptive; duration 13 day average (range 7 to 24 days).

Pistillate flowers: Occur mostly as doubles produced terminally on spurs, some (less than 10%) produced laterally on longer shoots. Presence of pistillate flowers on young trees observed in the forth growing season; moderately abundant on young trees, abundant on mature trees. Time of first pistillate flower receptivity early mid-season on average, 7 days (range 3 to 10 days) after full bloom of 'Delicious' apple (*Malus domestica*); average duration 15 days (range 10 to 26 days) with flowers produced terminally on spurs blooming ahead of those produced laterally on shoots. Coincidence of staminate and pistillate bloom averages 10 days (range 5 to 19 days); considered partially dichogamous and does best with an early pollen shedding cultivar.

Crop: Bears regularly; productivity low without cross pollination, medium with cross pollination (parent tree had produced up to 5,250 grams of nuts under conditions favorable for moderate cross-pollination, instant trees have not been exposed to conditions favorable for cross-pollination and yields have been less than 500 grams per tree); tendency to carry parthenocarpic fruit almost to maturity. Ripens in late September to early October (earliest and latest harvest dates September 20 and October 10, respectively).

Fruit: Subglobose and sutured; medium sized (average: length 4.46 centimeters; cheek to cheek 4.38 centimeters; suture plant 3.90 centimeters). Hull fleshy, smooth, glabrous, yellow-green (144A) with numerous conspicuous white dots; moderately thick, dehiscent, opening from apex to base in no particular pattern.

Nut: Roundish oblong, compressed (average: length 3.66 centimeters; cheek to cheek 3.48 centimeters; suture plant 3.00 centimeters); apex slightly to moderately beaked; basal end rounded; medium sized (101 nuts per kilogram, 46 per pound).

Shell: Thin (1.3 millimeters thick), moderately hard, well sealed; surface relatively smooth with shallow veins and furrows; color light brown (yellow-orange 22C). Diaphragm moderately thick and rigid, particularly at the basal end. Cavity well filled, kernel tight and difficult to remote in halves.

Kernel: Moderately small to medium sized (average for halves: length 2.94 centimeters, width 2.74 centimeters, thickness 1.10 centimeters), plump, convolutions moderate and even. Average kernel percentage: 52%. Pellicle light yellowish brown (yellow-orange 22C), semi-glossy, somewhat astringent, some speckling, and lightly veined. Richly flavored, oily; quality good.

Tree appears resistant to disease. Leaves are relatively tolerant to potato leafhopper (*Empoasca fabae*) damage.

The Persian walnut tree and its nuts herein described may vary in slight detail due to climate and soil conditions under the cultivar may be grown; the present description being of the cultivar as grown in Ames, Iowa.

I claim:

1. A new and distinct, cold-resistant cultivar of Persian walnut tree named 'Domoto' substantially as shown and described that withstands exposure to minus 35.6 degrees Celsius with minimal shoot injury, produces catkins that withstand exposure to minus 32 degrees Celsius, that is of small stature, and produces, on average, nuts that are larger than those produces by 'Hansen' (unpatented) Persian walnut.

* * * * *